United States Patent [19]

Bosslet et al.

[11] Patent Number: 5,639,621
[45] Date of Patent: Jun. 17, 1997

[54] MONOCLONAL ANTIBODIES AGAINST TUMOR-ASSOCIATED ANTIGENS

[75] Inventors: Klaus Bosslet; Peter Pfleiderer, both of Marburg; Gerhard Seemann, Marburg-Elnhausen, all of Germany

[73] Assignee: Behringwerke Aktiengesellschaft, Marburg, Germany

[21] Appl. No.: 468,661

[22] Filed: Jun. 6, 1995

Related U.S. Application Data

[62] Division of Ser. No. 957,827, Oct. 8, 1992, abandoned.

[30] Foreign Application Priority Data

Oct. 11, 1991 [DE] Germany ............... 41 33 791.3

[51] Int. Cl.$^6$ ............... C12N 5/12; C07K 16/30; A61K 39/395
[52] U.S. Cl. ............... 435/7.23; 530/387.1; 530/388.1; 435/70.21; 435/172.2; 435/69.6; 435/172.3; 435/252.3; 424/155.1; 424/133.1
[58] Field of Search ............... 424/137.1, 138.1, 424/139.1, 155.1, 174.1, 184.1, 185.1, 277.1, 70.21, 9.1; 435/69.6, 70.21, 172.2, 172.3, 240.27, 7.1, 7.23; 530/300, 350, 387.7, 388.8, 388.85, 389.7

[56] References Cited

FOREIGN PATENT DOCUMENTS

| 141079 | 5/1985 | European Pat. Off. . |
|---|---|---|
| 0239400 | 9/1987 | European Pat. Off. . |
| 0256654A2 | 2/1988 | European Pat. Off. . |
| 0376746A2 | 7/1990 | European Pat. Off. . |
| 0388914A1 | 9/1990 | European Pat. Off. . |
| 0397419A2 | 11/1990 | European Pat. Off. . |
| 0420394A1 | 4/1991 | European Pat. Off. . |
| 0443599A2 | 8/1991 | European Pat. Off. . |
| 3825615 | 2/1990 | Germany . |

OTHER PUBLICATIONS

Buchegger et al., "Monoclonal Antibodies Identify a CEA Crossreacting Antigen of 95 kD (NCA-95) Distinct in Antigenicity and Tissue Distribution From the Previously Described NCA of 55 kD", Int. J. Cancer, 33:643–649, (1984).

Bosslet et al., "Quantitative considerations supporting the irrelevance of of circulating serum CEA for the immunoscintigraphic visualization of CEA expressing carcinomas", Eur.J. Nucl. Med., 14:523–528 (1988).

Güssow et al., "Humanization of Monoclonal Antibodies", Methods in Enzymology, 203:99–121 (1991).

Saragovi et al., "Design and Synthesis of a Mimetic from an Antibody Complementarity–Determining Region", Science, 253:792–795 (1991).

Tijssen, "The immobilization of immunoreactants on solid phases", Practice & Theory of Enzyme Immunoassays, pp. 297–328, (1984).

Kufe et al., "Differential Reactivity of a Novel Monoclonal Antibody (DF3) with Human Malignant versus Benign Breast Tumors", Hybridoma, 3(3): 223–232, (1984).

Burchell, et al., Cancer Research, vol. 47, pp. 5476–7482, Oct. 15, 1987.

Kabat et al., "Sequence of Proteins of Immunological Interest", 4th Ed., US Department of Health and Human Services, US Government Printing Office (1987).

Sambrook, Fritsch, Maniatis, "Molecular Cloning, A Laboratory Manual", Cold Spring Harbor Laboratory, pp. 11–44, 51–127, 133–134, 141, 146, 150–167, 170, 188–193, 197–199, 248–255, 270–294, 310–328, 364–401, 438–506 (1982).

(List continued on next page.)

*Primary Examiner*—Lila Feisee
*Assistant Examiner*—Julie E. Reeves
*Attorney, Agent, or Firm*—Finnegan, Henderson, Farabow, Garrett & Dunner, L.L.P.

[57] ABSTRACT

The invention relates to monoclonal antibodies against a tumor-associated antigen which is mainly derived from tumors from the group of carcinomas of the breast, ovaries and prostate, as well as adenocarcinomas of the lung, which additionally react with polymorphic epithelial mucin (PEM), to the preparation and use thereof and to the use of the epitope defined by the antibody for diagnosis and therapy.

8 Claims, 17 Drawing Sheets

OTHER PUBLICATIONS

Sambrook Fritsch, Maniatis, "Molecular Cloning, A Laboratory Manual", Cold Spring Harbor Press, pp. 16.20–16.22, 16.30–16.40, 16.54–16.55 (1989).

Wirth et al., "Isolation of overproducing recombinant mammalian cell lines by a fast and simple selection procedure", Gene 73: 419–426 (1988).

Hieter et al., "Evolution of Human Immunoglobulin k J Region Genes*", The Journal of Biological Chemistry, 257(3): 1516–1522 (1982).

Shimizu et al., "Isolation and Characterization of Mucin–Like Glycoprotein in Human Milk Fat Globule Membrane", J. Biochem., 91:515–524 (1982).

Girling et al., "A Core Protein Epitope of the Polymorphic Epithelial Mucin Detected by the Monoclonal Antibody SM–3 is selectively Exposed in a Range of Primary Carcinomas", Int. J. Cancer, 43:1072–1067 (1989).

Taylor–Papadimitriou et al., "Monoclonal Antibodies to Epithelium–Specific Components of the Human Milk Fat Globule Membrane: Production and Reaction with Cells in Culture", Int. J. Cancer, 28:17–21 (1981).

Gosling, "A Decade of Development in Immunoassay Methodology", Clin. Chem., 36(8):1408–1427 (1990).

Cordell et al.,"Immuoenzymatic Labeling of Monoclonal Antibodies Using Immune Complexes of Alkaline Phosphatase and Monoclonal Anti–alkaline Phosphatas (APAAP Complexes)", Journal of Histochemistry and Cytochemistry, 32(2):219–229 (1984).

Orlandi et al., "Cloning immunoglobulin variable domains for expression by the polymerase chain reaction", Proc.Nat.Acad.Sci.USA, 86:3833–3837(1989).

Sanger et al., "DNA sequencing with chain–terminating inhibitors", Proc. Natl. Acad. Sci. USA, 74(12):5463–5467 (1977).

Miller et al., "Monoclonal Antibody Therapeutic Trials in Seven Patients With T–Cell Lymphoma", Blood, 62(5):988–995 (1983).

Joseph et al., "In vivo labelling of granulocytes with $^{99m}$Tc anti–NCA monoclonal anti–bodies for imaging inflammation", Eur. J. Nucl. Med., 14:367–373 (1988).

Jones et al., "Replacing the complementarity–determining regions in a human antibody with those from a mouse", Nature, 321:522–525 (1986).

Reichmann et al., "Reshaping human antibodies for therapy", Nature, 332:323–327 (1988).

Verhoeyen et al., "Reshaping Human Antibodies: Grafting an Antilysozyme Activity", Science, 239:1534–1536 (1988).

Hanisch et al., "Monoclonal Antibody BW385 Defines a Site–specific Thomsen–Friedenreich Disaccharide Linked to Threonine within the VTSA Motif of MUC1Tandem Repeats", Cancer Research, 55:4036–4040, (Sep. 1995).

Seaver et al 1994 Genetic Engineering vol. 14(14) pp. 10 +12.

Burchell et al 1989 Int. J. Cancer vol. 44:691–696.

Layton et al 1990 Tumor Biology vol 11:274–286.

Burchell et al Cancer Research 1987 vol. 47:5476–5482.

Paul, W.E. 1993 Fundamental Immunology p. 242.

```
       10                    30                    50
    L  Q  S  L  R  A  L  V  Q  P  G  G  S  M  K  L  S  C  V  A
    CTGCAGAGTCTGAGAGCCTTGGTGCAACCTGGAGGATCCATGAAACTCTCCTGTGTTGCC 70                    90                    110
    S  G  F  T  F  S  N  Y  W  M  N  W  V  R  Q  S  P  E  K  G
    TCTGGATTCACTTTCAGTAACTACTGGATGAACTGGGTCCGCCAGTCTCCAGAGAAGGGG 130                   150                   170
    L  E  W  V  A  E  I  R  L  K  S  N  N  Y  A  T  H  Y  A  E
    CTTGAGTGGGTTGCTGAAATTAGATTGAAATCTAATAATTATGCAACACATTATGCGGAG 190                   210                   230
    S  V  K  G  R  F  T  I  S  R  D  D  S  K  S  S  V  Y  L  Q
    TCTGTGAAAGGGAGGTTCACCATCTCAAGAGATGATTCCAAAAGTAGTGTCTACCTGCAA 250                   270                   290
    M  N  N  L  R  A  E  D  T  G  I  Y  Y  C  I  R  E  T  V  F
    ATGAACAACTTAAGAGCTGAAGACACTGGCATTTATTACTGTATCAGGGAGACGGTTTTT 310                   330
    Y  Y  Y  A  M  D  Y  W  G  Q  G  T  T  V  T
    TATTACTATGCTATGGACTACTGGGGCCAAGGGACCACGGTCACC
```

```
        10                    30                    50
 Q  L  T  Q  S  P  P  S  V  P  V  T  P  G  E  S  V  S  I  S
CAGCTGACCCAGTCTCCACCCTCTGTACCTGTCACTCCTGGAGAGTCAGTATCCATCTCC 70                    90                   110
 C  R  S  S  Q  S  L  L  H  G  D  G  N  T  Y  L  Y  W  F  L
TGCAGGTCTAGTCAGAGTCTCCTGCATGGTGATGGCAACACTTACTTGTATTGGTTCCTG 130                   150                   170
 Q  R  P  G  Q  S  P  R  L  L  I  Y  R  M  S  N  L  A  S  G
CAGAGGCCAGGCCAGTCTCCTCGGCTCCTGATATATCGGATGTCCAACCTTGCCTCAGGA 190                   210                   230
 V  P  D  R  F  S  G  S  G  S  G  T  A  F  T  L  R  I  S  R
GTCCCAGACAGGTTCAGTGGCAGTGGGTCAGGAACTGCTTTCACACTGAGAATCAGTAGA 250                   270                   290
 V  E  A  E  D  V  G  V  Y  Y  C  M  Q  H  L  E  Y  P  F  T
GTGGAGGCTGAGGATGTGGGTGTTTATTACTGTATGCAACATCTAGAATATCCTTTCACG

310
 F  G  G  G  K  V  E  I
TTCGGAGGGGGCAAGGTGGAGATCA
```

FIG. 6
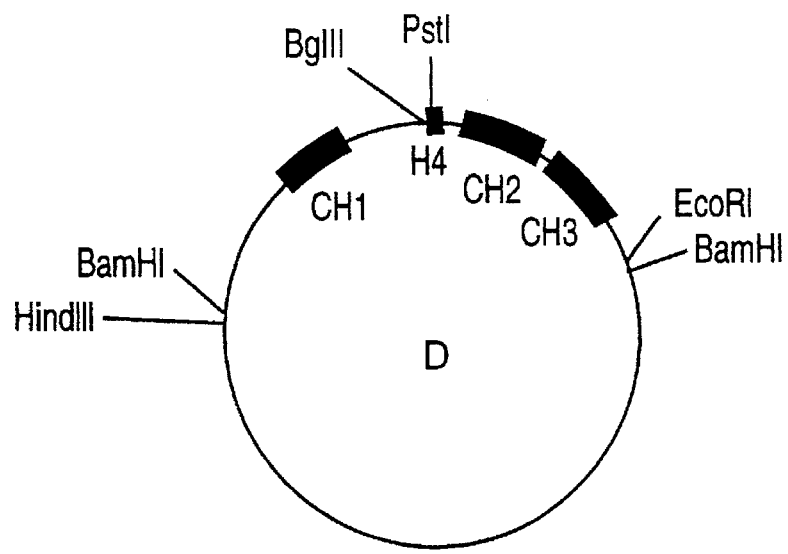
Bam HI PARTIAL
FILL IN
T4 LIGASE
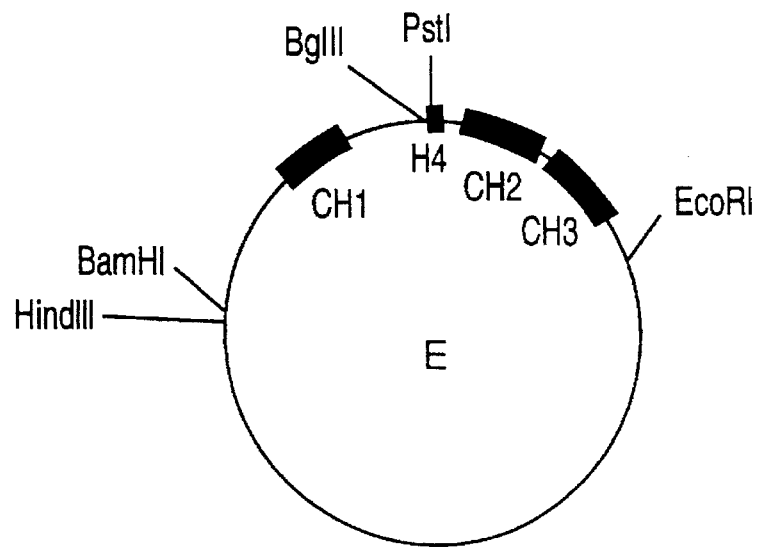

FIG. 10
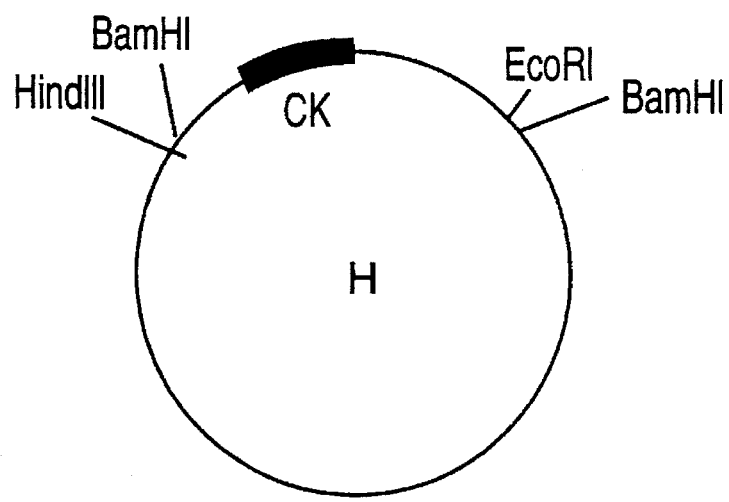
BamHI
FILL IN
RELIG.
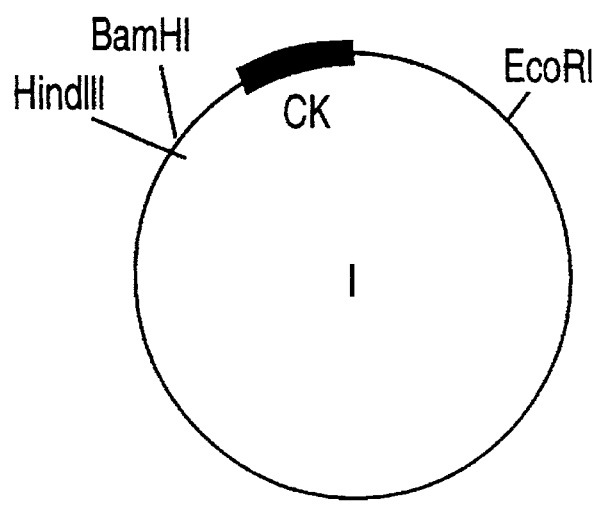

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Leu  Gln  Ser  Leu  Arg  Ala  Leu  Val  Gln  Pro  Gly  Gly  Ser  Met  Lys  Leu
 1              5                         10                        15

Ser  Cys  Val  Ala  Ser  Gly  Phe  Thr  Phe  Ser  Asn  Tyr  Trp  Met  Asn  Trp
               20                        25                        30

Val  Arg  Gln  Ser  Pro  Glu  Lys  Gly  Leu  Glu  Trp  Val  Ala  Glu  Ile  Arg
          35                   40                        45
```

-continued

```
    Leu  Lys  Ser  Asn  Asn  Tyr  Ala  Thr  His  Tyr  Ala  Glu  Ser  Val  Lys  Gly
         50                  55                      60

Arg  Phe  Thr  Ile  Ser  Arg  Asp  Asp  Ser  Lys  Ser  Ser  Val  Tyr  Leu  Gln
    65                       70                      75                            80

Met  Asn  Asn  Leu  Arg  Ala  Glu  Asp  Thr  Gly  Ile  Tyr  Tyr  Cys  Ile  Arg
                        85                      90                       95

Glu  Thr  Val  Phe  Tyr  Tyr  Tyr  Ala  Met  Asp  Tyr  Trp  Gly  Gln  Gly  Thr
                   100                 105                           110

Thr  Val  Thr
              115
```

( 2 ) INFORMATION FOR SEQ ID NO:2:

( i ) SEQUENCE CHARACTERISTICS:
    ( A ) LENGTH: 345 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:2:

```
CTGCAGAGTC  TGAGAGCCTT  GGTGCAACCT  GGAGGATCCA  TGAAACTCTC  CTGTGTTGCC    60

TCTGGATTCA  CTTTCAGTAA  CTACTGGATG  AACTGGGTCC  GCCAGTCTCC  AGAGAAGGGG   120

CTTGAGTGGG  TTGCTGAAAT  TAGATTGAAA  TCTAATAATT  ATGCAACACA  TTATGCGGAG   180

TCTGTGAAAG  GGAGGTTCAC  CATCTCAAGA  GATGATTCCA  AAAGTAGTGT  CTACCTGCAA   240

ATGAACAACT  TAAGAGCTGA  AGACACTGGC  ATTTATTACT  GTATCAGGGA  GACGGTTTTT   300

TATTACTATG  CTATGGACTA  CTGGGGCCAA  GGGACCACGG  TCACC                   345
```

( 2 ) INFORMATION FOR SEQ ID NO:3:

( i ) SEQUENCE CHARACTERISTICS:
    ( A ) LENGTH: 108 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:3:

```
    Gln  Leu  Thr  Gln  Ser  Pro  Pro  Ser  Val  Pro  Val  Thr  Pro  Gly  Glu  Ser
    1                   5                   10                       15

Val  Ser  Ile  Ser  Cys  Arg  Ser  Ser  Gln  Ser  Leu  Leu  His  Gly  Asp  Gly
                   20                       25                        30

Asn  Thr  Tyr  Leu  Tyr  Trp  Phe  Leu  Gln  Arg  Pro  Gly  Gln  Ser  Pro  Arg
              35                       40                       45

Leu  Leu  Ile  Tyr  Arg  Met  Ser  Asn  Leu  Ala  Ser  Gly  Val  Pro  Asp  Arg
         50                  55                       60

Phe  Ser  Gly  Ser  Gly  Ser  Gly  Thr  Ala  Phe  Thr  Leu  Arg  Ile  Ser  Arg
    65                       70                       75                           80

Val  Glu  Ala  Glu  Asp  Val  Gly  Val  Tyr  Tyr  Cys  Met  Gln  His  Leu  Glu
                        85                       90                       95

Tyr  Pro  Phe  Thr  Phe  Gly  Gly  Gly  Lys  Val  Glu  Ile
                   100                 105
```

( 2 ) INFORMATION FOR SEQ ID NO:4:

( i ) SEQUENCE CHARACTERISTICS:
    ( A ) LENGTH: 325 base pairs
    ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:4:

| | | | | | | |
|---|---|---|---|---|---|---|
| CAGCTGACCC | AGTCTCCACC | CTCTGTACCT | GTCACTCCTG | GAGAGTCAGT | ATCCATCTCC | 60 |
| TGCAGGTCTA | GTCAGAGTCT | CCTGCATGGT | GATGGCAACA | CTTACTTGTA | TTGGTTCCTG | 120 |
| CAGAGGCCAG | GCCAGTCTCC | TCGGCTCCTG | ATATATCGGA | TGTCCAACCT | TGCCTCAGGA | 180 |
| GTCCCAGACA | GGTTCAGTGG | CAGTGGGTCA | GGAACTGCTT | TCACACTGAG | AATCAGTAGA | 240 |
| GTGGAGGCTG | AGGATGTGGG | TGTTTATTAC | TGTATGCAAC | ATCTAGAATA | TCCTTTCACG | 300 |
| TTCGGAGGGG | GCAAGGTGGA | GATCA | | | | 325 |

MONOCLONAL ANTIBODIES AGAINST TUMOR-ASSOCIATED ANTIGENS

This is a division of application Ser. No. 07/957,827, filed Oct. 8, 1992, abandoned.

The invention relates to monoclonal antibodies against a tumor-associated antigen which is mainly derived from tumors from the group of carcinomas of the breast, ovaries and prostate, as well as adenocarcinomas of the lung, which additionally react with polymorphic epithelial mucin (PEM), to the preparation and use thereof and to the use of the epitope defined by the antibody for diagnosis and therapy.

Hybridoma technology has made it possible to prepare specific monoclonal antibodies (MAbs) even against unpurified antigens. This fact has made it possible to identify a large number of tumor-associated antigens (TAAs) which occur on certain human tumors but also on normal human tissues. Examples of such TAAs are CEA (carcinoembryonic antigen), N-CAM (neural cell adhesion molecule) and PEM (polymorphic epithelial mucin).

CEA is mainly expressed on adenocarcinomas of the gastrointestinal tract, N-CAM is located on tumors derived from neuroectoderm, and PEM occurs mainly on carcinomas of the breast and ovaries. The TAAs which have just been mentioned are high molecular weight glycoproteins which carry a large number of immunogenic epitopes for the murine immune system. Comparative immunohistochemical investigations on cryopreserved human tissues demonstrate that the specificity of an MAb which recognizes with its idiotype (V region) an epitope I on a TAA may show a different tissue binding than an MAb which recognizes an epitope II (Buchegger et al. (1984), Int. J. Cancer 33: 643–649).

Multifarious reasons are possible for this observation: crypticity of epitopes in certain tissues, cross-reactive epitopes on different antigens, changes in conformation of antigens on secretion from tissues into the plasma (Bosslet et al. (1988), Eur. J. Nucl. Med. 14: 523–528) etc. It may be concluded from this that the specificity of an MAb is not unambiguously given by the definition of the recognized antigen but is given by the exact description of the V region of the MAb in conjunction with its immunohistochemical specificity for cryopreserved human tissues and its serum specificity with circulating TAA structures in human serum or plasma. Thus, for example, a number of MAbs against the PEM which was isolated by Shimizu from human milk, (Shimizu, M. and Yamauchi, K. (1982), J. Biochem. 91, 515–524) have been developed and bind to different epitopes and, accordingly, have different properties (Girling et al. (1989), 43, 1072–1076, Taylor-Papadimitriou et al. (1981), Int. J. Cancer, 28, 17–21).

Certain anti-PEM MAbs (HMFG 1,2) show a strong reaction with human carcinomas of the breast and ovaries but also react significantly with normal human tissues (Taylor-Papadimitriou et al. (1981)). Other MAbs (SM 3, Girling et al. (1989)) react more weakly and heterogeneously with carcinomas of the breast and ovaries but, on the other hand, do not bind significantly to normal human tissue.

We have succeeded, surprisingly, in producing an anti-PEM MAb which reacts strongly with carcinomas of the breast, ovaries and prostate, as well as adenocarcinomas of the lung, binds only weakly to normal human tissue and, in addition, is able to detect PEM very specifically in human serum or plasma. Methods for the immunochemical determination of antigen are known to the person skilled in the art (see Gosling (1990), Clin. Chem. 36/8, 1408–1427). In this connection a distinction is made essentially between two classes: homogeneous assays such as, for example, particle-enhanced nephelometry or turbidimetry and heterogeneous methods, also called solid-phase assays.

Solid-phase assays are designed so that the analyte antigen is immobilized out of the sample to be investigated by a trapping antibody bound to a solid phase, and the immobilized antigen is detected by a second antibody provided with a detectable labeling moiety (conjugate). Detectable labels of this type are known to the person skilled in the art, and examples are enzymes, chemiluminescent or electrochemilumineseent, radioactive or else colored labels.

The hybridoma cell line BW 835 which produces the monoclonal antibody BW 835 was deposited on Oct. 11, 1991, at DSM, Deutsche Sammlung von Mikroorganismen und Zellkulturen GmbH, Mascheroder Weg 1b, D-3300 Braunschweig, under the number DSM ACC2022.

Antibodies within the meaning of this invention also mean antibody fragments.

BRIEF DESCRIPTION OF THE DRAWINGS

FIG. 1a is the nucleic acid sequence of BW 835 $V_H$.

FIG. 1b is the nucleic acid sequence of BW 835 $V_K$.

FIG. 6 shows the cloning of plasmid D to obtain plasmid E. See Example 5.

FIG. 10 shows the partial cleavage of clone H to obtain plasmid I. See Example 9.

Figure 2:
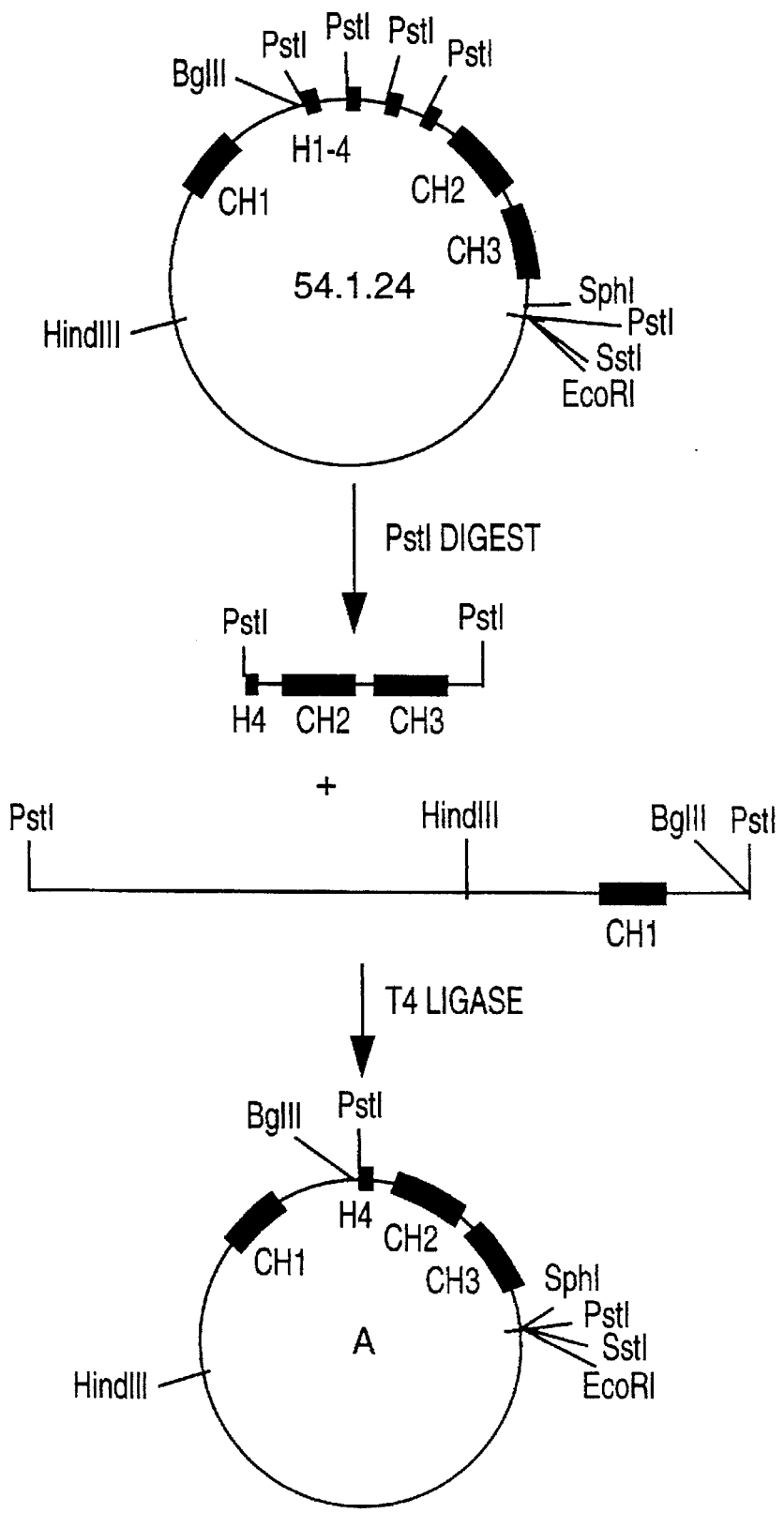
FIG. 2 shows the cloning of plasmid A which harbors a human $IgG_3\Delta C$ gene in which the H1, H2 and H3 exons have been deleted. See Example 1.

The preparation and the properties of this MAb (BW 835) are described below:

The MAb was generated by immunizing Balb/c mice with the MCF-7 and SW-613 breast carcinoma cell lines by methods known from the literature (EP-A2-0 141079).

The distribution of the epitope defined by the MAb BW 835 on cryopreserved human carcinomas and normal human tissues is shown in Tables Ia and b respectively, comparing with the MAb SM-3 (Girling et al. 1989). The data are based on an immunohistochemical detection with the APAAP technique (Cordell at al. (1984), J. Histochem. Cytochem. 32, 219). It can clearly be seen that MAb BW 835 reacts strongly with all 15 carcinomas of the breast from 15 tested carcinomas of the breast, whereas the MAb SM-3 detects only 11 of 15 carcinomas of the breast.

In the case of carcinoma of the ovaries, the MAb BW 835 reacts strongly with 6 of 8 tested tumors, and the MAb SM-3 reacts with a few cells in 6 of 8 carcinomas. With all the other carcinoma types tested, especially the adenocarcinomas of the lung and the carcinomas of the prostate, MAb BW 835 shows a quantitatively stronger reaction. These data show that MAb BW 835 detects more carcinomas with a quantitatively stronger reaction than the MAb SM-3 disclosed in the literature.

The binding of MAb BW 835 to normal human tissue is shown in Table Ib. The APAAP technique was employed to obtain the data in this case too. The epitope defined by MAb BW 835 is expressed significantly on the ductal epithelium of the breast and the ductal epithelium of the pancreas, and is weakly expressed on the surface epithelium of the lungs, on some nerve fibers and on the collecting tubules and the glomeruli of the kidney. All the other tested normal tissues are negative.

Because of its high selectivity, the MAb BW 835 can also be used as inducer for internal image anti-paratope MAbs. MAbs of this type might be employed as epitope vaccine for the therapy of human tumors.

The demonstration that the epitope defined by the MAb BW 835 is located on the PEM defined by MAb SM-3 was checked by a double-determinant assay.

Spleen
  Negative
Colon
  Negative
Stomach
  Mucosa and some mucin-containing ducts with positive reaction
Lung
  Surface epithelium of the lung with weak positive reaction
Kidney
  Some glomeruli weakly stained, positive apical staining of the collecting tubules
Brain
  Negative
Peripheral nerve
  Some nerve fibers weakly stained
Bone marrow
  Negative
Peripheral blood components
  Lymphocytes, monocytes, granulocytes, erythrocytes, platelets are negative The MAb BW 835 used as trap was able to trap from cell culture supernatants of the T47 cell line an antigen which was detectable by the enzyme-labeled MAb SM-3. Furthermore, in the Western blot both MAbs stain molecules which correspond to the molecular weight position of PEM.

Once the immunological specificity data for the MAb BW 835 were defined, the mRNA was isolated from $10^8$ hybridoma cells which secrete the MAb BW 835, the V genes of the heavy and light chains of the MAbBW 835 were isolated TABLE Ia Binding of the MAb BW 835 to cryopreserved human tumors

| MAb | Human tumor type | | | | | |
|---|---|---|---|---|---|---|
| | Carcinomas of the breast pos./total | Ovarian carcinomas pos./total | Prostate carcinomas pos./total | Stomach carcinomas pos./total | Colon carcinomas pos./total | Pancreas carcinomas pos./total |
| BW 835 | 15/15 | 6/8 | 4°/5 | 4*/6 | 3*/4 | 4*/7 |
| SM 3 | 11/15 | 6*/8 | 1°/5 | 3*/6 | 1°/4 | 3°/7 |

| MAb | Lung carcinomas | | | |
|---|---|---|---|---|
| | SCLC pos./total | adeno pos./total | Squamonus cell pos./total | Large cell pos./total |
| BW 835 | 4*/10 | 11°/12 | 5*/11 | 7°/11 |
| SM 3 | 2*/10 | 6*/12 | 4*/11 | 3*/11 |

*a few cells positive
°a few areas of secreted products positive

Table Ib

Binding of the MAb BW 835 to cryopreserved normal human tissue
Tissue type:
Mammary gland
  Positive reaction with the acinar epithelium, positive apical staining of the epithelium in the ducts and in some secreting vesicles
Ovary
  Negative
Pancreas
  Positive apical staining in the ducts
Liver
  Negative by the method described by Orlandi et al. (1989), Proc. Natl. Acad. Sci. U.S.A.: 86, 3833–3837, and the nucleic acid sequence of the essential regions of the V gene exons were determined by the method described by Sanger et al. (1977), Proc. Natl. Acad. Sci., U.S.A.: 74, 5463–5467 (FIGS. 1a, b) (SEQ ID NS:1–4).

On repeated high-dose administration of MAbs of murine origin, such as, for example, the MAb BW 835, for in vivo therapy of humans it is possible to immunize the patients. They are able to produce human anti-mouse immunoglobulin antibodies (HAMA) after about 10–14 days (Miller et al., (1983), Blood, 62, 988; Joseph et al., (1988), European Journal of Nuclear Medicine, 14, 367). These HAMAs may have unfavorable effects on the pharmacokinetics and pharmacodynamics of the MAb and impede continuation of the treatment.

In order to reduce the immunogenicity of xenogenic antibodies as far as possible, a technique in which only the CDR loops of the $V_L$ and $V_H$ domains of the xenogenic antibodies are transferred to $V_L$ and $V_H$ domains of human antibodies has been developed (Jones, P. T., et al., (1986), Nature, 321, 522) (EP-A-87302620, G. Winter), and this process is called "humanization" and takes place at the level of the $V_H$ and $V_L$ genes.

The technical procedure for humanization of an antibody is divided essentially into three sections: the cloning and nucleic acid sequence analysis of the specific $V_H$ and $V_L$ genes, the computer-assisted design of the synthetic oligonucleotides for the transfer of the CDR loops to the human $V_H$ and $V_L$ domains and the transfer of the CDR loops to human $V_H$ and $V_L$ domains by specific mutagenesis (Riechmann, L., et al., (1988), Nature, 332, 323; Verhoeyen, M., et al., (1988), Science, 239, 1534).

Humanization of this type can also be carried out on MAb BW 835 in order to improve its usability in vivo. This would entail the authentic CDR regions of the BW 835 $V_H$ and $V_L$ domains (defined by Kabat, E. A., et al. (1987) Sequences of Proteins of Immunological Interest, fourth edition, U.S. Dept. of Health and Human Services, U.S. Government Printing Office) or CDR regions with a few modified amino acids being transferred to human $V_H$ and $V_L$ domains, it being possible for a few amino acids of the framework regions located between the CDR regions to be taken over from the mouse antibody to the humanized antibody in order to minimise the change in the antigen-binding properties of the resulting MAb BW 835 in the humanized form.

The variable domains of the humMAb BW 835 are accordingly composed of the framework regions, which are authentic or modified at a few points, of the variable domains of a human MAb onto which the CDR regions which are authentic or have been modified at a few amino-acid positions of the mouse MAb BW 835 have been transplanted.

The following examples describe the steps necessary for cloning and nucleic acid sequence analysis of the V genes and for the expression of BW 835 specificity as chimeric MAb. The techniques used in Examples 1–12 were, unless otherwise indicated, taken from Molecular Cloning, a Laboratory Manual; Sambrook, Fritsch, Maniatis; Cold Spring Harbor Laboratory, 1982 (pages 11–44, 51–127, 133–134, 141, 146, 150–167, 170, 188–193, 197–199, 248–255, 270–294, 310–328, 364–401, 437–506) and from Molecular Cloning, A Laboratory Manual, Second Edition; Sambrook, Fritsch, Maniatis; Cold Spring Harbor Laboratory Press, 1989 (pages 16.2–16.22, 16.30–16.40, 16.54–16.55).

EXAMPLE 1

The plasmid clone 54.1.24 which harbors the human IgG$_3$ΔC gene (FIG. 2) (DE-A1-38 25 615, FIG. 2) was cleaved with PstI. The vector resulting from this was ligated to the largest of the resulting PstI insert fragments and transformed into bacteria. The plasmid clone A which harbors a human IgG$_3$ΔC gene in which the H1, H2 and H3 exons have been deleted (IgG3Δ) was identified by restriction analysis and nucleic acid sequence determination.

EXAMPLE 2

Figure 3:
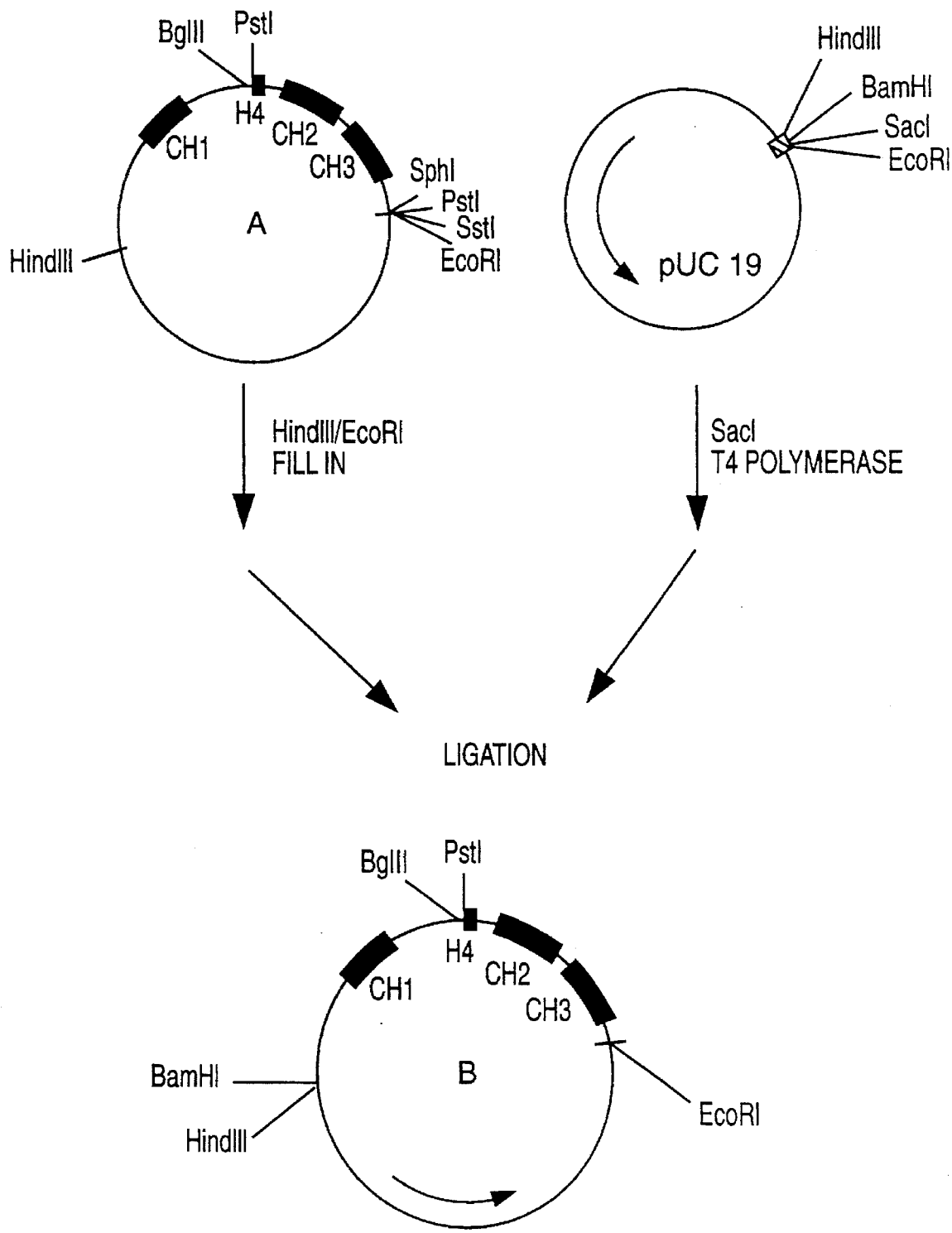
FIG. 3 shows the cloning of plasmid B. See Example 2.

The plasmid clone A was cleaved with HindIII and EcoRI, the ends were filled in with Klenow polymerase, the IgG$_3$Δ insert was isolated and ligated into a pUC19 vector cleaved with SstI and provided with blunt ends with the aid of T$_4$ polymerase. A plasmid clone B in which the IgG$_3$Δ gene is orientated so that the HindIII cleavage site is located at the 5' end and the EcoRI cleavage site is located at the 3' end of the pUC19 polylinker was identified by restriction mapping and nucleic acid sequence analysis (FIG. 3).

EXAMPLE 3

Figure 4:
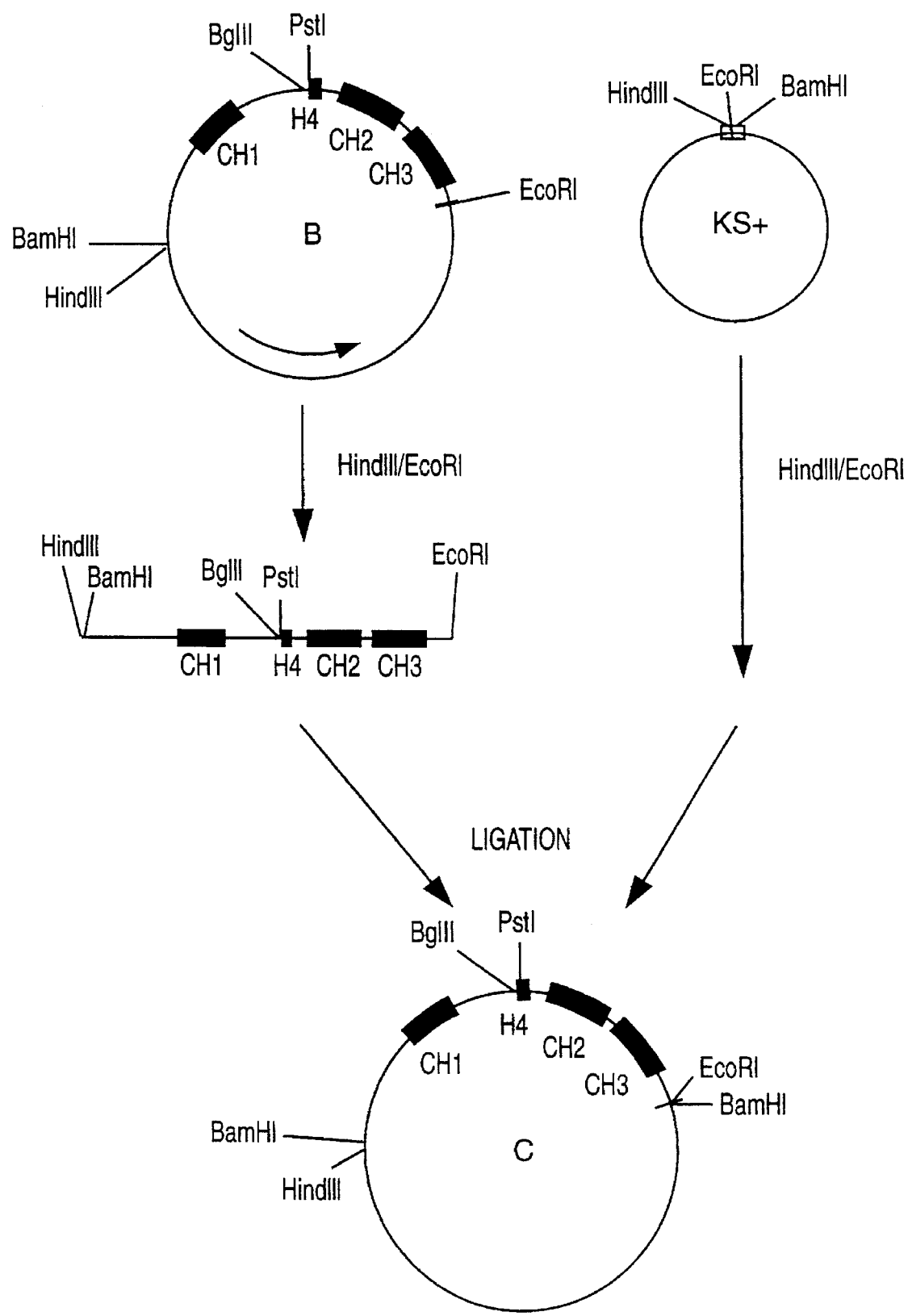
FIG. 4 shows the cloning of plasmid C. See Example 3.

The plasmid clone B was cleaved with EcoRI and HindIII, the IgG$_3$Δ insert was isolated and ligated into a KS+plasmid vector (pBluescriptII KS+; Stratagene, La Jolla, Calif.) likewise cleaved with HindIII and EcoRI. The plasmid clone C in which the IgG$_3$Δ gene is flanked at the 5' and at the 3' end by a BamHI cleavage site was isolated (FIG. 4).

EXAMPLE 4

Figure 5:
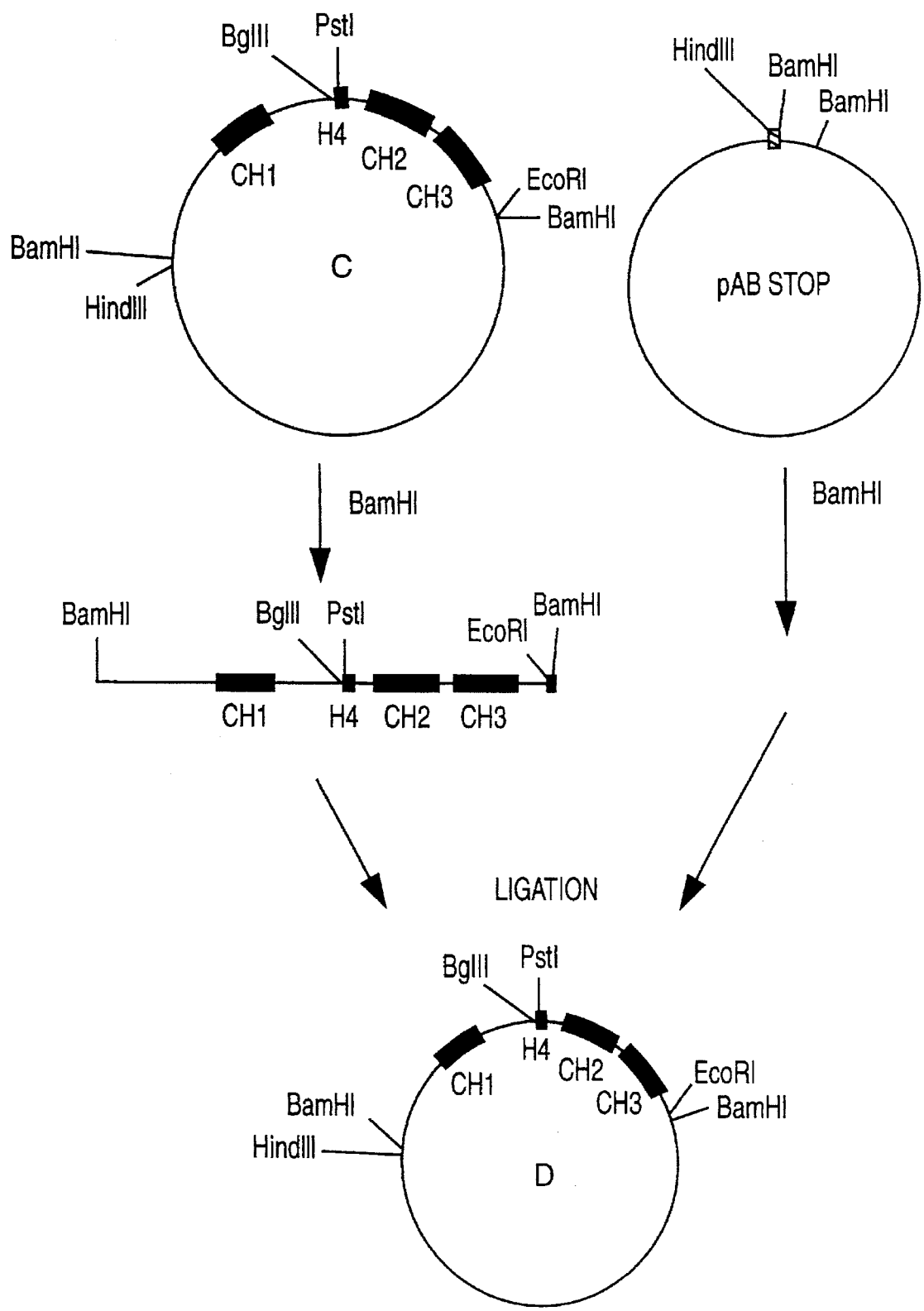
FIG. 5 shows the cloning of plasmid D. See Example 4.

The plasmid clone C was cleaved with BamHI, the IgG$_3$Δ insert was isolated and ligated into the expression vector pABStop (Wirth et al. (1988), Gene, 73, 419–426) likewise cleaved with BamHI. The expression plasmid D which contains the IgG$_3$Δ C gene in the orientation shown in FIG. 5 was identified. In this cloning the pABStop vector loses the polyadenylation signal and SV40 stop located between the two BamHI cleavage sites.

EXAMPLE 5

The expression plasmid D was partially cleaved with BamHI, the ends were filled in with Klenow polymerase and religated. The expression plasmid E in which the BamHI cleavage site 3' from the IgG$_3$Δ gene is destroyed was isolated (FIG. 6).

EXAMPLE 6

Figure 7:
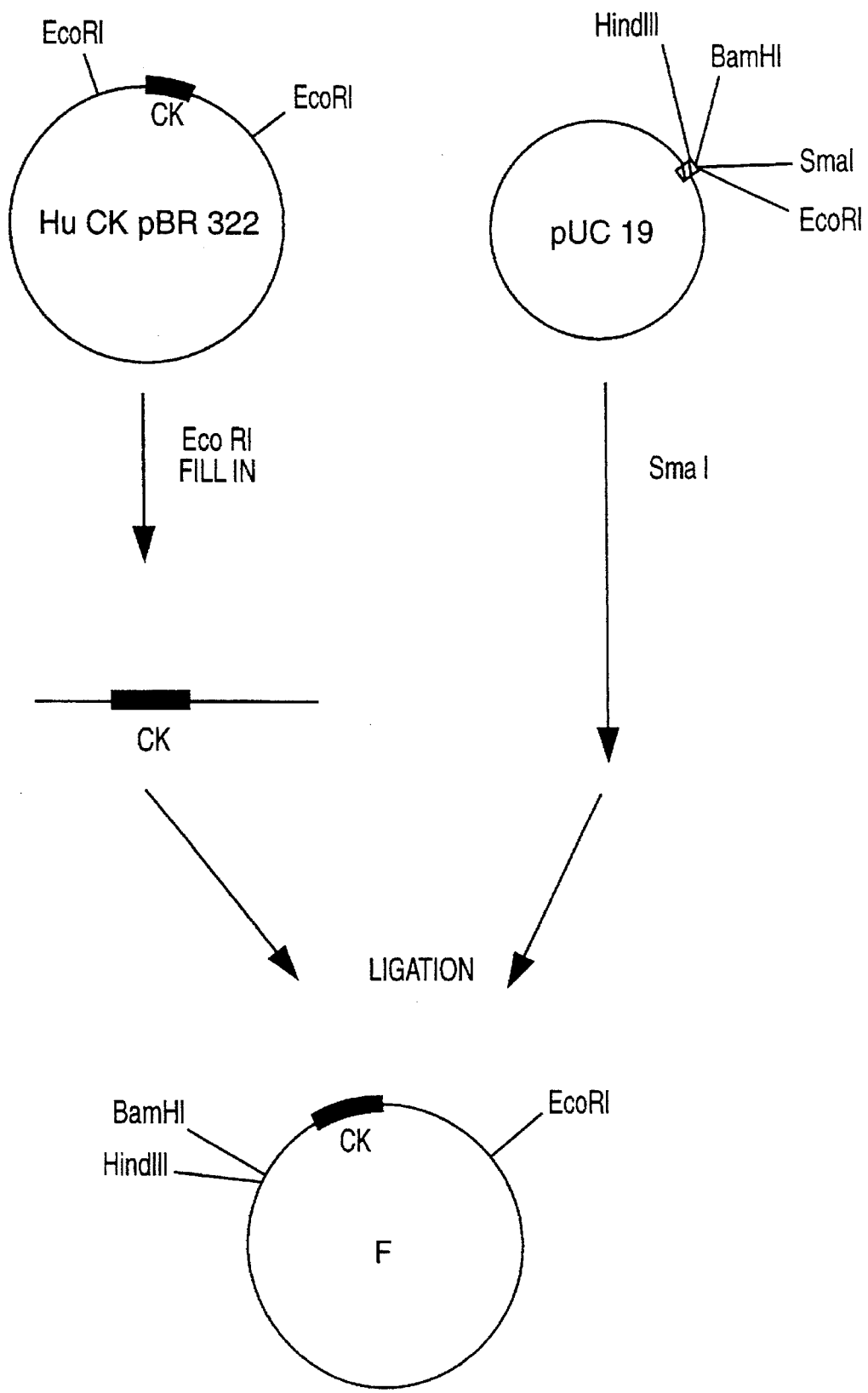
FIG. 7 shows the isolation of plasmid F. See Example 6.

The human C kappa gene (Hieter et al. (1982), J. Biol. Chem., 257, No. 3, 1516–1522) was obtained as EcoRI fragment cloned in pBR 322 from Prof. P. Leder, Harvard Medical School. The pBR322 vector was cleaved with EcoRI, the EcoRI cleavage sites were filled in, the C kappa insert was isolated and ligated into a pUC19 vector cleaved with SmaI. The plasmid clone F in which the C kappa gene is flanked at the 5' end by a HindIII after a BamHI cleavage site and at the 3' end by an EcoRI cleavage site was isolated (FIG. 7).

EXAMPLE 7

Figure 8:
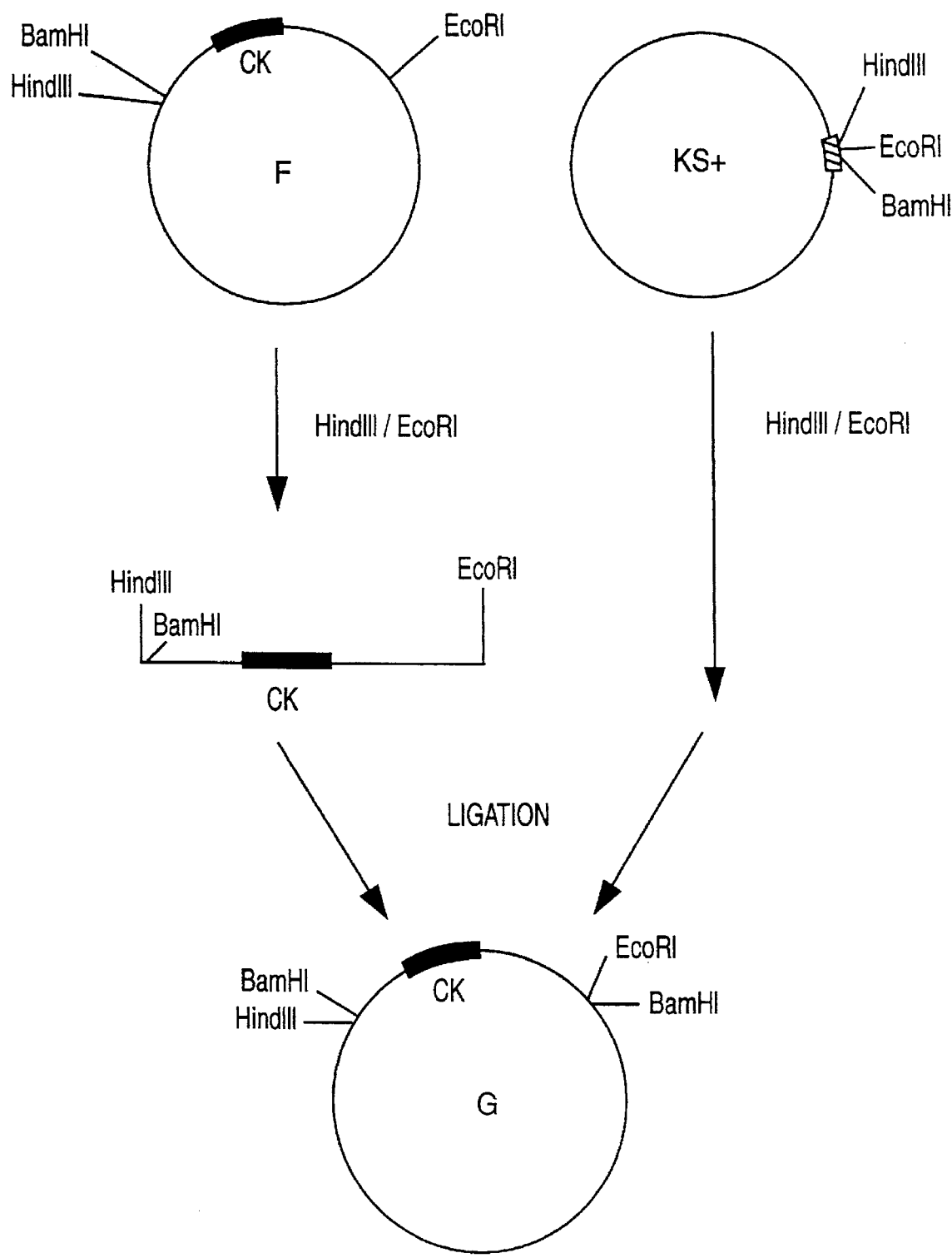
FIG. 8 shows the cleavage of plasmid F to obtain plasmid G. See Example 7.

The plasmid clone F was cleaved with HindIII and EcoRI, the C kappa insert was isolated and cloned into a HindIII/EcoRI-cleaved KS+ plasmid. The phasmid clone G in which the C kappa insert is flanked at the 5' and at the 3' end by a BamHI cleavage site was isolated (FIG. 8).

EXAMPLE 8

Figure 9:
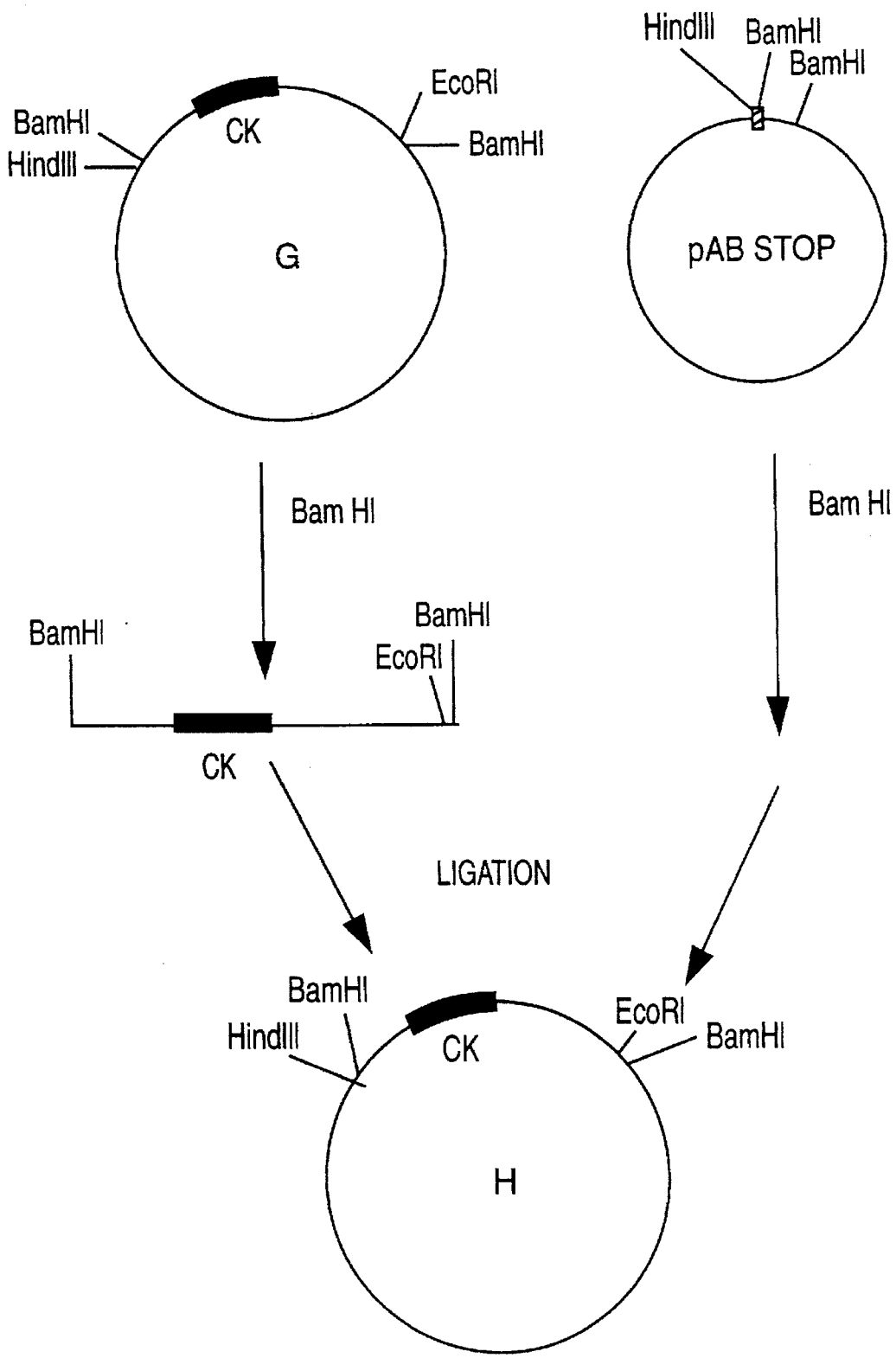
FIG. 9 shows the cleavage of plasmid E to obtain plasmid H. See Example 8.

The plasmid clone G was cleaved with BamHI, the C kappa insert was isolated and cloned into a pAB stop vector cleaved with BamHI. The clone H in which the C kappa gene is orientated so that the HindIII cleavage site of the pAB stop vector is located at its 5' end was identified by restriction mapping and nucleic acid sequence analysis (FIG. 9).

EXAMPLE 9

The clone H was partially cleaved with BamHI, the restriction ends were filled in and religated. The clone I in which the BamHI cleavage site 3' of the C kappa gene is destroyed was identified by restriction mapping (FIG. 10).

EXAMPLE 10

Figure 11A:
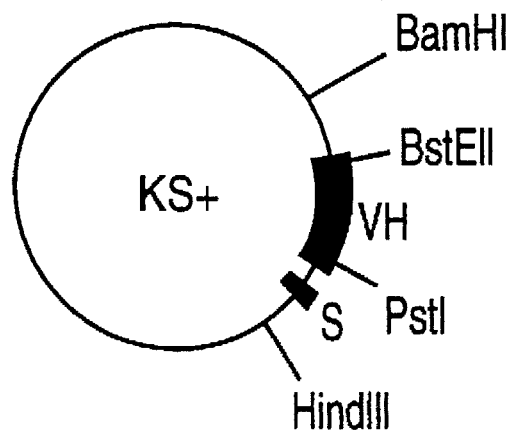
FIG. 11a shows the restriction cleavage sites for MAb BW 835 $V_H$. See Example 12.
Figure 11B:
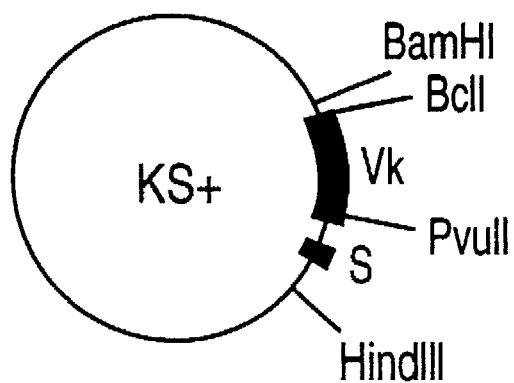
FIG. 11b shows the restriction cleavage sites for Mab BW 835 $V_K$. See Example 12.
Figure 12:
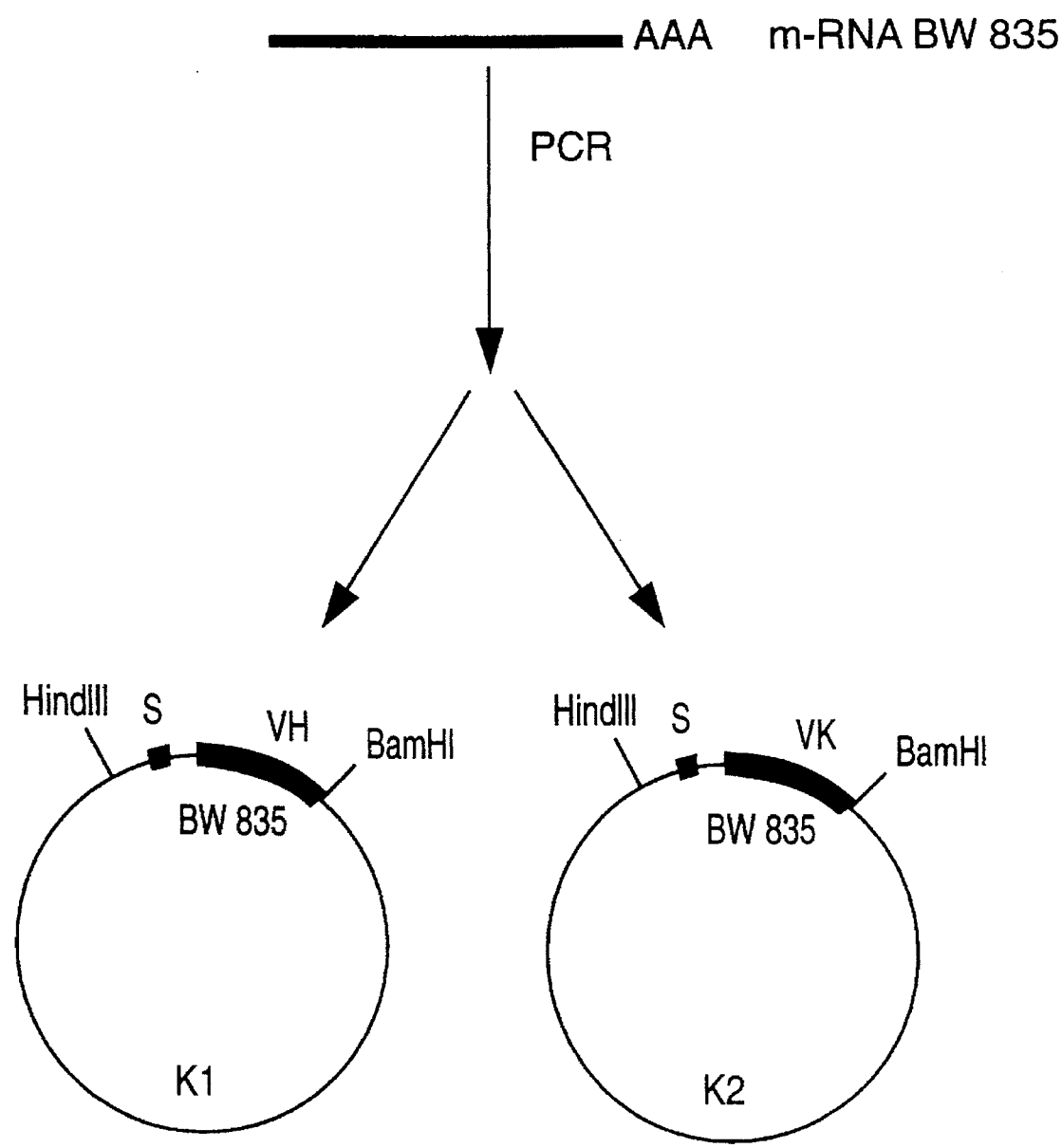
FIG. 12 shows the isolation of plasmids K1 and K2. See Example 10.

The $V_H$ and $V_K$ genes of the MAb BW 835 were amplified using the PCR technique and specific oligonucleotides by the method of Orlandi et al. (1989) and cloned in KS+ vectors (Güssow and Seemann (1991), Methods in Enzymology, Vol. 203) which contained $V_H$ and $V_K$ genes with suitable restriction cleavage sites (FIG. 11a for $V_H$ and FIG. 11b for $V_K$). The clones K1 and K2 which contain the $V_H$ (K1) and $V_K$ (K2) genes of the MAb BW 835 were isolated (FIG. 12).

EXAMPLE 11

The nucleic acid sequences of the $V_H$ and $V_K$ genes of the MAb BW 835 from the clones K1 and K2 were determined by the method of Sanger et al. (1977) (FIGS. 1a, b) (SEQ ID NOS:1-4). It is possible to generate mimetics based on the CDRs from this sequence by the method described by Saragovi et al. (Saragovi et al. (1991), Science 253, 792-795).

Figure 13:
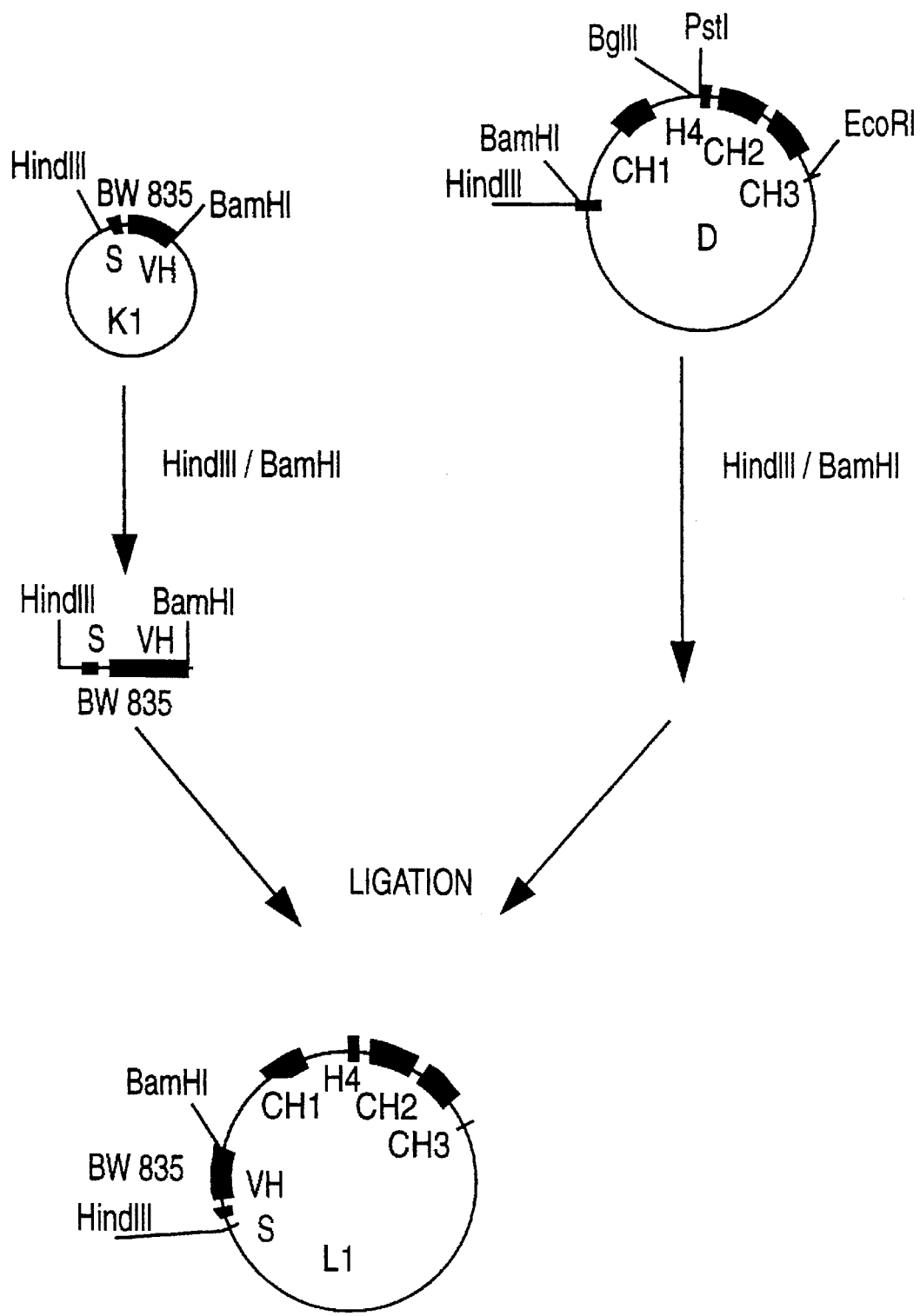
FIG. 13 shows the expression vector L1. See Example 11.
Figure 14:
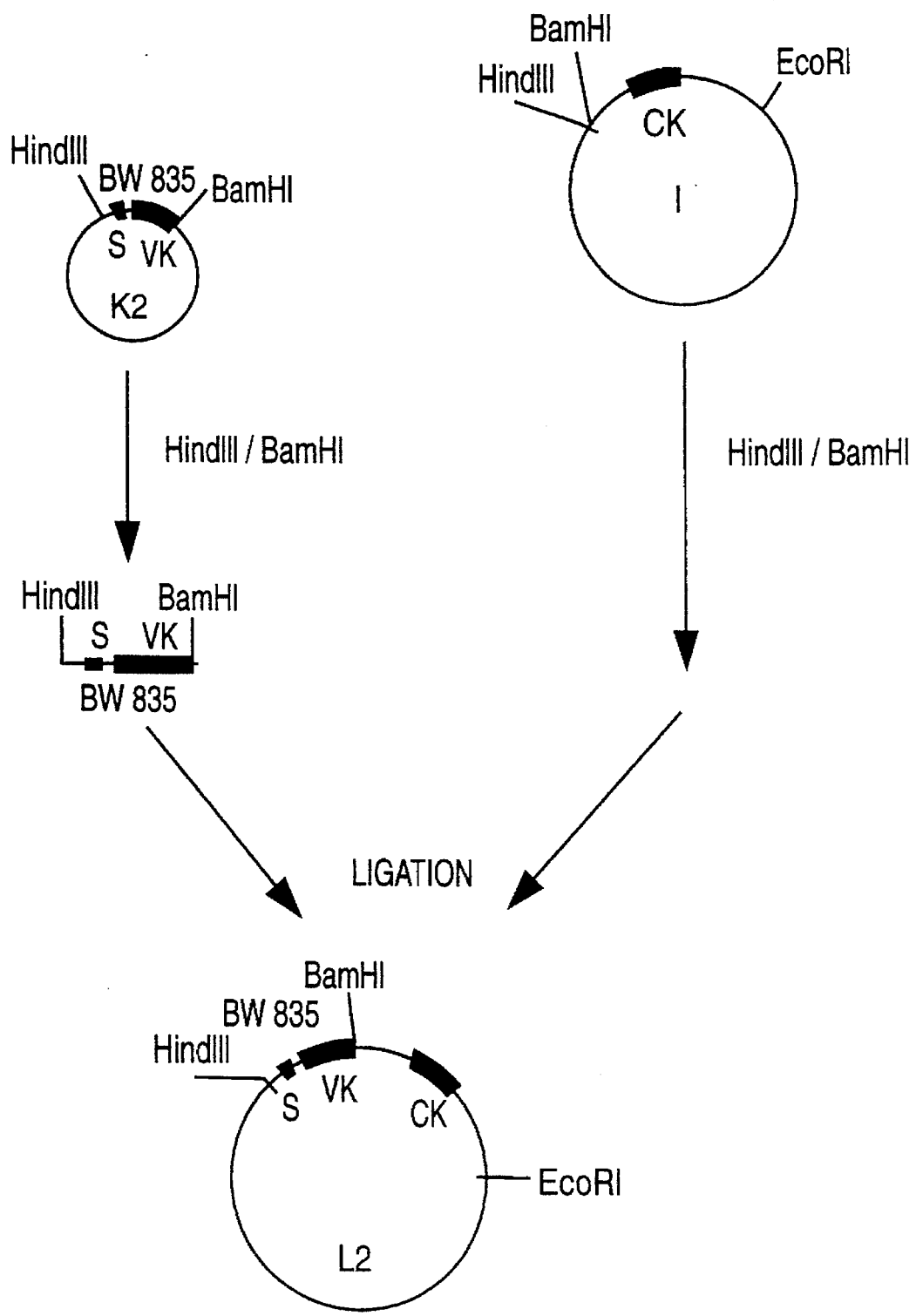
FIG. 14 shows the expression vector L2. See Example 11.

Furthermore, the $V_H$ and $V_K$ gene inserts were cut out of the clones K1 and K2 with the aid of the restriction endonucleases HindIII and BamHI and were cloned into the vectors D ($V_H$) and I ($V_K$) likewise cleaved with HindIII and BamHI. The expression vectors L1 and L2 which contain immunoglobulin heavy (L1) (FIG. 13) and light (L2) (FIG. 14) chain genes with the V genes of MAb BW 835 were isolated. The expression vectors L1 and L2 can be used for the expression of a chimeric MAb with the specificity of MAb BW 835.

Examples 12 and 13 are intended to explain the use of the MAb BW 835 for serodiagnosis of malignant tumors.

EXAMPLE 12

The MAb BW 835 was bound by adsorption to the walls of wells of microtiter plates (NUNC) by methods knownto the person skilled in the art (Tijssen, P., "Practice and theory of enzyme immunoassay" Elsevier (1988), 297-328). 10 µl of sample were pipetted into each of the wells prepared in this way and each containing 100 µl of buffer (OSND, Behringwerke) and incubated at +37° C. for 2 hours. After washing three times with diluted Enzygnost washing buffer (OSEW, Behringwerke), 100 µl of MAb BW 835 (1 µg/ml) which was conjugated to peroxidase by known methods were introduced into each of the individual wells. The following 2-hour incubation step at +37° C. was completed by a cycle of three washes. Subsequently, for the third incubation step at room temperature, 100 µl of a buffer/ substrate chromogen solution (OUVG/OUVF, Behringwerke) were pipetted into each of the wells, and the enzyme reaction was stopped after 30 minutes with 100 µl of Enzygnost stop solution (OSFA, Behringwerke). The extinction of the samples was determined as 450 nm.

Figure 15:
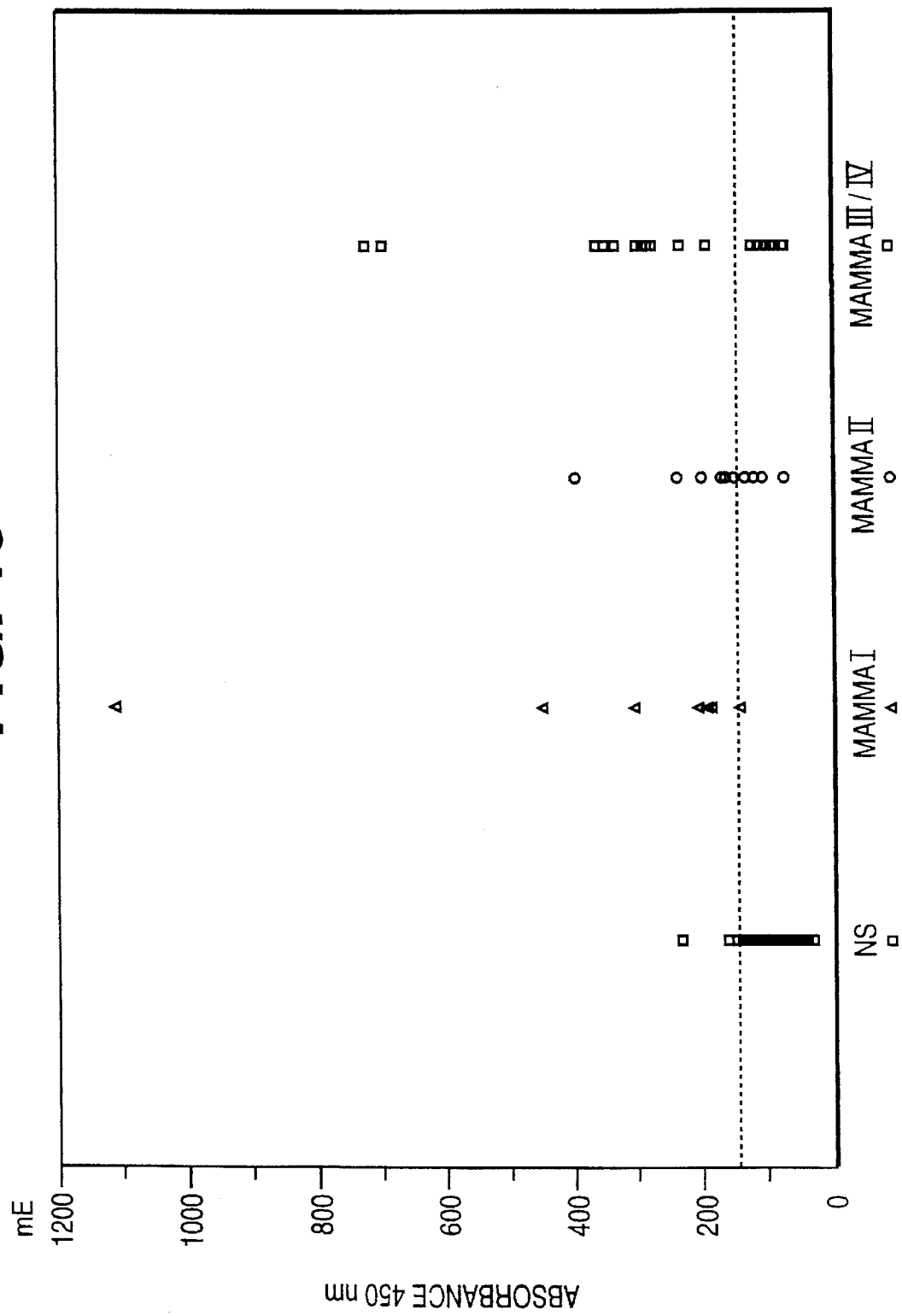
FIG. 15 compares the concentration of antigen bound by MAb BW 835 in serum or plasma of patients with malignant tumors with that in healthy patients. See Example 12.

Result:

The extinctions determined in this way correspond in the level thereof to the concentration of the antigen in the sample. The concentration of the antigen defined by the specific binding of MAb BW 835 in serum or plasma of patients with malignant tumors is distinctly raised by comparison with that in healthy patients (FIG. 15). This particularly applies to patients with late-stage carcinoma of the breast, but also, surprisingly, to those with early-stage carcinoma who, with other commercial tumor marker tests for detecting breast cancer-associated antigens in serum (for example CA 15-3), by comparison give false-negative findings significantly more often, and thus overall better sensitivities were found for the homologous version described.

EXAMPLE 13

It is also possible to use for the detection of PEM in serum in the double-determinant assay in combination with the MAb BW 835 other peroxidase-labeled antibodies which recognize further epitopes on the tumor-associated antigens defined by MAb BW 835. To do this, for example, a test analogous to Example 12 was carried out using the DF3 antibody disclosed in the literature (Kufe et al. (1984), Hybridoma 3, 223) in peroxidase-labeled form (CA 15-3- Test, Boehringer Mannheim) as conjugate component.

Figure 16:
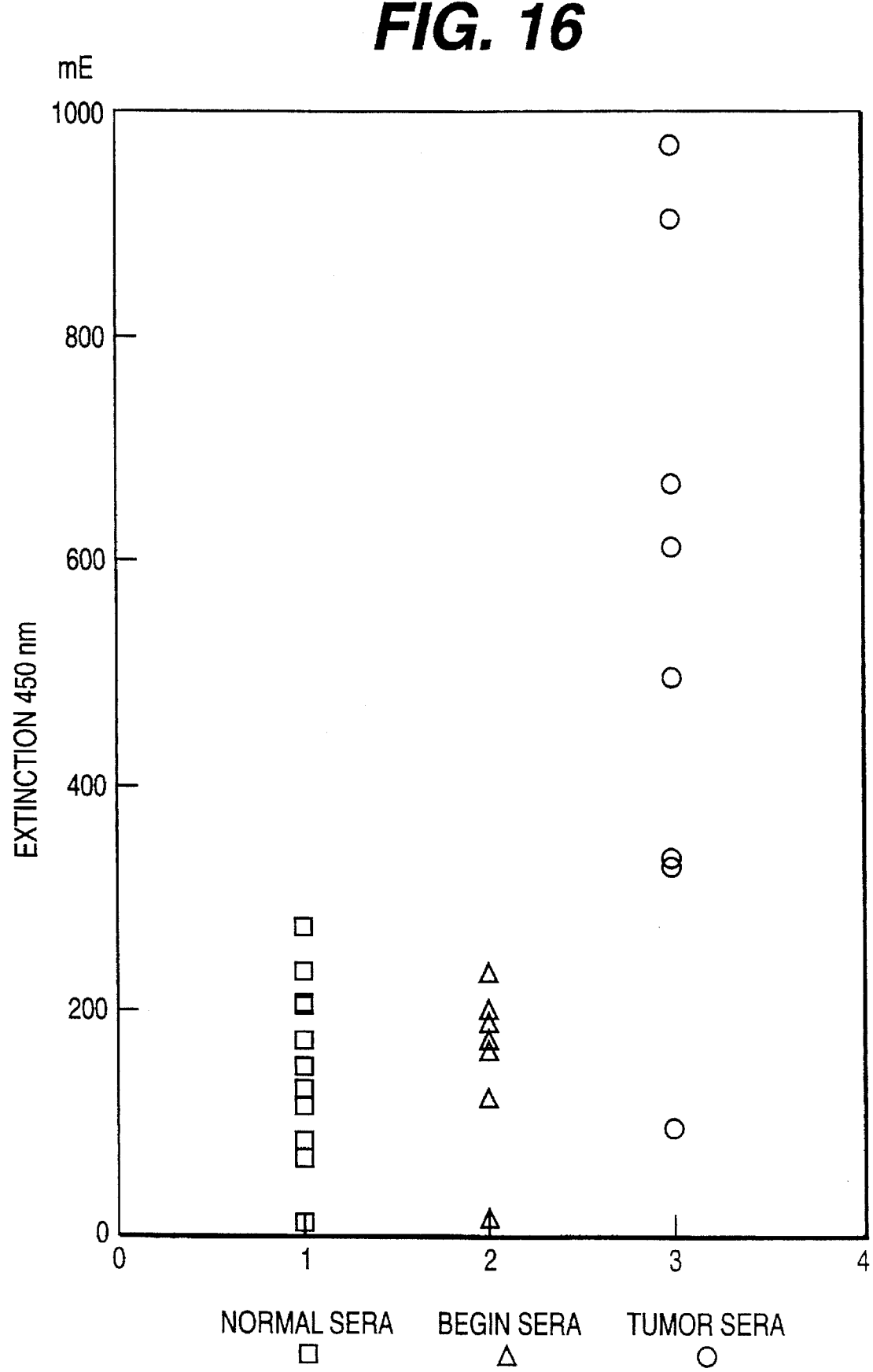
FIG. 16 compares the use of peroxidase-labeled $DF_3$, antibody conjugate with MAb BW 835 to recognize further epitopes to the tumor-associated antigens defined MAb BW 835 tumor sera, normal sera, and sera from patients with benign diseases. See Example 13.

Result:

The use of, for example, DF3-POD as conjugate component to supplement the solid-phase-bound BW 835 produced distinctly higher serum values for the tumor sera compared with a normal serum pool and patients with benign diseases, which once again underlines the potential of the MAb BW 835 as specific component for a tumor marker test (FIG. 16).

---

We claim:

1. An in vitro diagnostic aid comprising a monoclonal antibody, BW 835, which is produced by the hybridoma cell line DSM ACC2022, wherein the monoclonal antibody is immunoreactive with a polymorphic epithelial mucin (PEM) antigen associated with tumors selected from the group consisting of breast carcinomas, ovarian carcinomas, prostate carcinomas and lung adenocarcinomas.

2. An in vitro diagnostic aid comprising a modified antibody that contains the CDR regions of the variable domains of BW 835 represented by SEQ ID No: 1 and SEQ ID No: 3, wherein the modified antibody is immunoreactive with a polymorphic epithelial mucin (PEM) antigen associated with tumors selected from the group consisting of breast carcinomas, ovarian carcinomas, prostate carcinomas and lung adenocarcinomas.

3. An in vitro diagnostic aid comprising a modified antibody that comprises the CDR regions of the variable domains of BW 835 represented by SEQ ID No: 1 and SEQ ID No: 3, wherein the CDR regions are grafted onto a human framework and wherein the modified antibody is immunoreactive with a polymorphic epithelial mucin (PEM) antigen associated with tumors selected from the group consisting of breast carcinomas, ovarian carcinomas, prostate carcinomas and lung adenocarcinomas.

4. The in vitro diagnostic aid according to claim 3 wherein the framework region is modified in order to minimize the change in antigen binding properties of the antibody BW 835.

5. A diagnostic aid for detecting tumor-associated antigens in biological samples comprising a monoclonal antibody, BW 835, which is produced by the hybridoma cell line DSM ACC2022, wherein the monoclonal antibody is immunoreactive with a polymorphic epithelial mucin (PEM) antigen associated with tumors selected from the group consisting of breast carcinomas, ovarian carcinomas, prostate carcinomas and lung adenocarcinomas.

6. A diagnostic aid for detecting tumor-associated antigen in biological samples comprising a modified antibody that contains the CDR regions of the variable domains of BW 835 represented by SEQ ID No: 1 and SEQ ID No: 3, wherein the modified antibody is immunoreactive with a polymorphic epithelial mucin (PEM) antigen associated with tumors selected from the group consisting of breast carcinomas, ovarian carcinomas, prostate carcinomas and lung adenocarcinomas.

7. A diagnostic aid for detecting tumor-associated antigens in biological samples comprising a modified antibody that comprises the CDR regions of the variable domains of BW 835 represented by SEQ ID No: 1 and SEQ ID No: 3, wherein the CDR regions are grafted onto a human framework and wherein the modified antibody is immunoreactive with a polymorphic epithelial mucin (PEM) antigen associated with tumors selected from the group consisting of breast carcinomas, ovarian carcinomas, prostate carcinomas and lung adenocarcinomas.

8. The diagnostic aid according to claim 7 wherein the framework region is modified in order to minimize the change in antigen binding properties of the antibody BW 835.

* * * * *